(12) United States Patent
Cristiano et al.

(10) Patent No.: US 12,290,582 B2
(45) Date of Patent: May 6, 2025

(54) CREAMY HYDRATING COSMETIC COMPOSITION IN A WATER RELEASE EMULSION

(71) Applicant: L'OREAL, Paris (FR)

(72) Inventors: Michele Cristiano, Old Bridge, NJ (US); Noah Wieder, Linden, NJ (US); Mark Zaw, Iselin, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/560,328

(22) Filed: Dec. 23, 2021

(65) Prior Publication Data

US 2023/0201088 A1   Jun. 29, 2023

(51) Int. Cl.
*A61K 8/06* (2006.01)
*A61K 8/34* (2006.01)
*A61K 8/37* (2006.01)
*A61K 8/44* (2006.01)
*A61Q 19/00* (2006.01)

(52) U.S. Cl.
CPC .............. *A61K 8/064* (2013.01); *A61K 8/345* (2013.01); *A61K 8/37* (2013.01); *A61K 8/44* (2013.01); *A61Q 19/00* (2013.01); *A61K 2800/30* (2013.01); *A61K 2800/591* (2013.01)

(58) Field of Classification Search
None
See application file for complete search history.

(56) References Cited

U.S. PATENT DOCUMENTS

| | | | | |
|---|---|---|---|---|
| 8,758,736 | B2 * | 6/2014 | Lorant | .................... A61K 8/064 424/70.13 |
| 2021/0145708 | A1 | 5/2021 | Han et al. | |

FOREIGN PATENT DOCUMENTS

| | | | | |
|---|---|---|---|---|
| CN | 105411866 | A | 3/2016 | |
| EP | 3574760 | A1 * | 12/2019 | ............. A01N 47/44 |
| FR | 2917609 | A1 | 12/2008 | |
| WO | 2018114214 | A1 | 6/2018 | |

OTHER PUBLICATIONS

Paula's Choice, Dicaprylyl Carbonate in Skin Care: What It Is webage, https://www.paulaschoice.com/ingredient-dictionary/ingredient-dicaprylyl-carbonate.html (Year: 2023).*
Cremer, C3H8O3 | Glycerine Info—Cremer Oleo, https://web.archive.org/web/20220522082214/https://www.cremeroleo.de/en/products/glycerine/c3h803.html (Year: 2022).*
Search Report issued to French counterpart Application No. FR2201205 dated Oct. 18, 2022.
Anonymous, Mintel, "Mineral Multi-Defense Sunscreen Fluid SPF 50+" Record ID No. 8728891, Jun. 2021, wwww.gnpd.com.
Anonymous, Mintel, "Mineral Multi-Defense Tinted Sunscreen Fluid SPF 50+" Record ID No. 8728947, Jun. 2021, wwww.gnpd.com.

* cited by examiner

*Primary Examiner* — David J Blanchard
*Assistant Examiner* — Edwin Coleman Mitchell
(74) *Attorney, Agent, or Firm* — McNees Wallace & Nurick LLC

(57) ABSTRACT

A cosmetic composition in the form of a creamy emulsion having an internal water phase in an oil phase includes at least one polyglyceryl ester, a glutamic acid, or a derivative thereof, at least one cosmetically acceptable glycol or diol, at least one oil, water, and optionally one or more additives. The composition excludes mineral and organic UV filters. The creamy emulsion demonstrates breaking and release of the water phase upon rubbing application of the composition on a substrate. The composition demonstrates stability at temperatures in a range from about 5° C. to about 45° C. for a period of eight weeks and under freeze-thaw conditions that range from about −20° C. to about 25° C., where the stability is evidenced by lack of separation of the water and oil phases and/or maintaining rheological characteristics over time in the absence of rubbing on a substrate.

19 Claims, No Drawings

CREAMY HYDRATING COSMETIC COMPOSITION IN A WATER RELEASE EMULSION

FIELD

This invention relates to a cosmetic composition, in particular a creamy water in oil emulsion that exhibits a fast, watery break during application.

BACKGROUND

Consumers seek cosmetic compositions that are formulated with sustainable, natural and/or green materials, and in particular that lack or minimize use of non-renewable ingredients (e.g., mineral oil and petrol based ingredients) and ingredients that have negative environmental impact. In some examples, consumers seek such compositions that also provide hydrating and moisturizing benefits with a pleasing texture, such as hydrating and moisturizing products that include high water content in an inverse or water in oil emulsion. A variety of products are available that include at least some of the desirable features sought by consumers, however, formulations that include high water content in an inverse or water in oil emulsion have been shown to be unstable for conventional use and storage, owing to the limitations of the emulsifier systems employed to retain the water phase in the oil phase. Thus, despite their otherwise desirable properties, such products may fail to meet the quality expectations of customers when the products break prior (i.e., release water phase from the oil phase and convert from a thick and creamy to a liquidous state) prior to application losing their thick and creamy texture and become thin and liquidous or leaving pools of water and/or oil phase in the container. Accordingly, there is a need for products that provide the environmental and sensorial properties that customers seek and maintain stability of texture during storage and under conditions of ordinary use.

SUMMARY

To address the deficiencies in the art with hydrating and moisturizing products, particularly those with high water phase content, the inventors provide a composition that has a unique fast, watery break from the emulsion releasing the large internal water phase quickly during application. The composition provides a substantially thick creamy initial texture transitioning to a thin texture, wherein the creamy emulsion is stabilized and not susceptible to separation under freeze-thaw and high temperature conditions, making it desirable from a quality perspective. Through this disclosure, the composition, as exemplified herein, encompasses various embodiments that are silicone-free, high quality inverse emulsion products capable of holding a large water phase content, greater than 75%, and having consumer pleasing texture. In various embodiments, the composition is formulated with sustainable, natural and/or green materials, and in particular that lack or minimize use of non-renewable ingredients and ingredients that have negative environmental impact.

In accordance with various embodiments, the disclosure provides a cosmetic composition, in the form of a creamy emulsion having an internal water phase in an oil phase, the creamy emulsion having i. at least one polyglyceryl ester;
  ii. glutamic acid, or a derivative thereof;
  iii. at least one cosmetically acceptable glycol or diol;
  iv. at least one oil;
  v. water; and,
  vi. optionally one or more additives.

In various embodiments, the composition excludes mineral and organic UV filters. And in various embodiments, the creamy emulsion demonstrates breaking and release of the water phase upon rubbing application of the composition on a substrate, and the composition demonstrates stability at temperatures in a range from about 5° C. to about 45° C. for a period of eight weeks and under freeze-thaw conditions that range from about −20° C. to about 25° C., where the stability is evidenced by lack of separation of the water and oil phases in the absence of rubbing on a substrate.

In some embodiments, the at least one polyglyceryl ester is selected from the group consisting of polyglyceryl-4 diisostearate/polyhydroxystearate/sebacate, polyglyceryl-6 polyricinoleate, polyglyceryl-3 diisostearate, polyglyceryl-2 oleate, polyglyceryl-10 laurate, polyglyceryl-3 oleate (and) diisostearoyl polyglyceryl-3 dimer dilinoleate, polyglyceryl-4 isostearate and combinations thereof. In some embodiments, the glutamic acid, or a derivative thereof is selected from the group consisting of tetrasodium glutamate diacetate, lauroyl glutamic acid, myristoyl glutamic acid, palmitoyl glutamic acid, stearoyl glutamic acid, behenoyl glutamic acid, olivoyl glutamic acid, cocoyl glutamic acid, the salts thereof, and combinations thereof. In some embodiments, the at least one oil is selected from the group consisting of Butyrospermum Parkii (Shea) Butter, Copernicia Cerifera (Carnauba) Wax, Persea Gratissima (avocado) oil, squalane, and combinations thereof. In some embodiments, the at least one cosmetically acceptable glycol or diol is selected from the group consisting of propanediol, ethylene glycol, propylene glycol, butylene glycol, pentylene glycol, hexylene glycol, decylene glycol, 1,2-butanediol, 1,2-heaxanediol, caprylyl glycol, ethyl hexanediol and combinations thereof.

In some embodiments, the at least one polyglyceryl ester is present from about 0.01% to about 2%, by weight of the composition.

In some embodiments, the glutamic acid, or a derivative thereof is present from about 0.1% to about 1.5% by weight of the composition. In some embodiments, the glutamic acid or derivative thereof may be in the oil phase or the water phase. In those embodiments wherein the glutamic acid includes tetrasodium glutamate diacetate, the tetrasodium glutamate diacetate is in the water phase.

In some embodiments, the at least one cosmetically acceptable glycol or diol is present from about 0.01% to about 10% by weight of the composition.

In some embodiments, the at least one oil is present from about 0.1% to about 23%, by weight of the composition.

In some embodiments, the cosmetically acceptable glycol or diol is present in an amount in a range from about 0.01% to about 10%, by weight of the composition, whereby under a given application strain when the composition is rubbed on a substrate, the creamy emulsion demonstrates breaking and release of the water phase more rapidly as the amount of the cosmetically acceptable glycol or diol is increased within the range.

In some embodiments, the water, or water and a water-based hydrating agent or solvent or combination thereof is present from about 75% to about 95% by weight of the composition, and wherein, when present, the at least one hydrating agent is present from about 1% to about 20% by weight of the composition.

In some embodiments, the composition is a water-in-oil emulsion comprising (a) a water phase that comprises the water, or water and a water-based hydrating agent or solvent or combination thereof, and the at least one cosmetically acceptable glycol or diol, the water phase present in a range of from about 75% to about 95% by weight, based on the weight of the composition, and (b) an oil phase comprising the at least one polyglyceryl ester, in some embodiments the glutamic acid, or a derivative thereof, and the at least one oil. In some embodiments, the composition has a ratio of the total weight of the water phase to the total weight of the at least one polyglyceryl ester in a range from about 45 to about 70. In some embodiments, the glutamic acid or derivative thereof may be in the oil phase or the water phase. In those embodiments wherein the glutamic acid includes tetrasodium glutamate diacetate, the tetrasodium glutamate diacetate is in the water phase.

In some embodiments, the oil phase further comprises one or more oils phase ingredients selected from the group consisting of oil-soluble active ingredients, emollients, silicone oils, and combinations thereof, and one or both the water and oil phases optionally includes one or more of the optional additives, the optional additives selected from the group consisting of pH adjusters, chelating agents, skin care actives, preservatives, fillers, powders, fragrances, dyes, pigments, and combinations thereof.

In accordance with some embodiments, the disclosure provides a cosmetic composition in which
i. the at least one polyglyceryl ester is present from about 0.01% to and not more than about 2%, by weight of the composition;
ii. the glutamic acid, or a derivative thereof is present from at least about 0.1% to about 1.5%, by weight of the composition;
iii. the at least one cosmetically acceptable glycol or diol is present from about 0.01% to about 10%, by weight of the composition;
iv. the at least one oil is present from about 0.1% to about 23%, by weight of the composition;
v. the water, or water and a water-based hydrating agent or solvent or combination thereof is present from about 65% to about 95% by weight of the composition; and,
vi. the optionally one or more additives is selected from the group consisting of pH adjusters, chelating agents, skin care actives, preservatives, fillers, powders, fragrances, dyes, pigments, and combinations thereof.

In some embodiments, the at least one polyglyceryl ester is selected from the group consisting of polyglyceryl-4 diisostearate/polyhydroxystearate/sebacate, polyglyceryl-6 polyricinoleate, polyglyceryl-3 diisostearate, polyglyceryl-2 oleate, polyglyceryl-10 laurate, polyglyceryl-3 oleate (and) diisostearoyl polyglyceryl-3 dimer dilinoleate, polyglyceryl-4 isostearate and combinations thereof. In some embodiments, the glutamic acid, or a derivative thereof is selected from the group consisting of tetrasodium glutamate diacetate, lauroyl glutamic acid, myristoyl glutamic acid, palmitoyl glutamic acid, stearoyl glutamic acid, behenoyl glutamic acid, olivoyl glutamic acid, cocoyl glutamic acid, the salts thereof, and combinations thereof. In some embodiments the at least one cosmetically acceptable glycol or diol is selected from the group consisting of propanediol, ethylene glycol, propylene glycol, butylene glycol, pentylene glycol, hexylene glycol, decylene glycol, 1,2-butanediol, 1,2-heaxanediol, caprylyl glycol, ethyl hexanediol and combinations thereof. In some embodiments, the at least one oil is selected from the group consisting of Butyrospermum Parkii (Shea) Butter, Copernicia Cerifera (Carnauba) Wax, Persea Gratissima (avocado) oil, squalane, and combinations thereof.

In some embodiments, the at least one polyglyceryl ester comprises polyglyceryl-4 diisostearate/polyhydroxystearate/sebacate, the glutamic acid, or a derivative thereof comprises tetrasodium glutamate diacetate, the at least one cosmetically acceptable glycol or diol comprises propanediol, and the at least one oil comprises Butyrospermum Parkii (Shea) Butter, Copernicia Cerifera (Carnauba) Wax, Persea Gratissima (avocado) oil, squalane, and the water, or water and a water-based hydrating agent or solvent or combination thereof comprises water, and at least one hydrating agent present from about 1% to about 20% by weight of the composition, all amounts by weight, based on the total weight of the composition.

In some embodiments, the at least one polyglyceryl ester comprises polyglyceryl-4 diisostearate/polyhydroxystearate/sebacate present at about 1.35%; the glutamic acid, or a derivative thereof comprises tetrasodium glutamate diacetate present at about 0.8%; the at least one cosmetically acceptable glycol or diol comprises propanediol present from about 1.6% to about 5%; the at least one oil comprises Butyrospermum Parkii (Shea) Butter, Copernicia Cerifera (Carnauba) Wax, Persea Gratissima (avocado) oil, and squalane, each present from about 0.1% to about 23%; and the water, or water and a water-based hydrating agent or solvent or combination thereof comprises water, and at least one hydrating agent that comprises glycerin present at about 5%. In some embodiments, the composition further comprises one or more additives selected from the group consisting of sodium dehydroacetate, salicylic acid, phenoxyethanol, chromium oxide greens, sodium PCA, copper gluconate, sodium chloride, tocopherol, caffeine, beta-carotene (beta carotene or other provitamin A carotenoid), retinol, citric acid, and combinations thereof.

In accordance with various embodiments, the disclosure also provides a method for applying a water breaking cosmetic composition. In some embodiments, the method includes steps that include: selecting a cosmetic composition in the form of a creamy emulsion having an internal water phase in an oil phase, the creamy emulsion including
i. at least one polyglyceryl ester;
ii. glutamic acid, or a derivative thereof;
iii. at least one cosmetically acceptable glycol or diol;
iv. at least one oil; and
v. water, or water and a water-based hydrating agent or solvent or combination thereof
and applying the composition to a keratinous substrate by contacting the composition and rubbing in a circular motion whereby the creamy emulsion demonstrates breaking and release of the water phase.

In some embodiments of the method the cosmetic composition is provided in which the composition excludes mineral and organic UV filters, and wherein, and wherein the composition demonstrates stability at temperatures in a range from about 5° C. to about 45° C. for a period of eight weeks and under freeze-thaw conditions that range from about −20° C. to about 25° C., stability evidenced by lack of separation of the water and oil phases in the absence of rubbing on a substrate In some embodiments of the method the cosmetic composition is provided in which the at least one polyglyceryl ester is present from about 0.01% to about 2%; the glutamic acid, or a derivative thereof is present from about 0.1% to about 1.5%; the at least one cosmetically acceptable glycol or diol is present from about 0.01% to about 10%; the at least one oil is present from about 0.1% to about 23%, by weight of the composition; and the water, or water and a water-based hydrating agent or solvent or combination thereof is present from about 65% to about 95%; all amounts by weight, based on the total weight of the composition. In some embodiments of the method the cosmetic composition is provided in which the composition optionally comprises one or more additives selected from the group consisting of pH adjusters, chelating agents, skin care actives, preservatives, fillers, powders, fragrances, dyes, pigments, and combinations thereof.

In some embodiments of the method the cosmetic composition is provided in which the at least one polyglyceryl ester comprises polyglyceryl-4 diisostearate/polyhydroxystearate/sebacate present at about 1.35%; the glutamic acid, or a derivative thereof comprises tetrasodium glutamate diacetate present at about 0.8%; the at least one cosmetically acceptable glycol or diol comprises propanediol present at about 1.6% to about 5%; the at least one oil is present from about 0.1% to about 23%, by weight of the composition; and the water, or water and a water-based hydrating agent or solvent or combination thereof comprises water present from about 65% to about 95% and glycerin present at about 5%. In some embodiments of the method the cosmetic composition is provided in which the composition further comprises one or more additives selected from the group consisting of sodium dehydroacetate, salicylic acid, phenoxyethanol, chromium oxide greens, sodium PCA, copper gluconate, sodium chloride, tocopherol, caffeine, beta-carotene (beta carotene or other provitamin A carotenoid), retinol, citric acid, and combinations thereof, and wherein by weight of the composition. In some embodiments of the method the cosmetic composition is provided in which the composition is a creamy water-in oil emulsion comprising (a) a water phase that comprises the water, or water and a water-based hydrating agent or solvent or combination thereof, and the at least one cosmetically acceptable glycol or diol, and (b) an oil phase comprising the at least one polyglyceryl ester, in some embodiments the glutamic acid, or a derivative thereof, and the at least one oil. In some embodiments of the method the cosmetic composition is provided in which the composition has a ratio of the total weight of the water phase to the total weight of the at least one polyglyceryl ester in a range from about 45 to about 70, and wherein the oil phase further comprises one or more oils phase ingredients selected from the group consisting of silicone oils, oil-soluble active ingredients, emollients, and combinations thereof. In some embodiments, the glutamic acid or derivative thereof may be in the oil phase or the water phase. In those embodiments wherein the glutamic acid includes tetrasodium glutamate diacetate, the tetrasodium glutamate diacetate is in the water phase.

In accordance with various embodiments, the disclosure also provides a method for preparing a cosmetic composition comprising a creamy emulsion having an internal water phase in an oil phase. In some embodiments, the method includes steps that include:

providing ingredients that exclude mineral and organic UV actives, the provided ingredients comprising:
  i. at least one polyglyceryl ester;
  ii. glutamic acid, or a derivative thereof;
  iii. at least one cosmetically acceptable glycol or diol;
  iv. at least one oil;
  v. water, or water and a water-based hydrating agent or solvent or combination thereof; and,
  vi. optionally one or more additives
and combining the provided ingredients to provide (a) a water phase that comprises the water, or water and a water-based hydrating agent or solvent or combination thereof, and the at least one cosmetically acceptable glycol or diol, and (b) an oil phase comprising the at least one polyglyceryl ester, in some embodiments the glutamic acid, or a derivative thereof, and the at least one oil. In some embodiments, the glutamic acid or derivative thereof may be in the oil phase or the water phase. In those embodiments wherein the glutamic acid includes tetrasodium glutamate diacetate, the tetrasodium glutamate diacetate is in the water phase.

In some embodiments of the method the cosmetic composition demonstrates stability at temperatures in a range from about 5° C. to about 45° C. for a period of eight weeks and under freeze-thaw conditions that range from about −20° C. to about 25° C., stability evidenced by lack of separation of the water and oil phases in the absence of rubbing on a substrate.

In some embodiments of the method the formed composition is a creamy water-in oil emulsion comprising (a) a water phase that comprises the water, or water and a water-based hydrating agent or solvent or combination thereof, and the at least one cosmetically acceptable glycol or diol, and (b) an oil phase comprising the at least one polyglyceryl ester, in some embodiments the glutamic acid, or a derivative thereof, and the at least one oil, wherein the oil phase further comprises one or more oils phase ingredients selected from the group consisting of oil-soluble active ingredients, emollients, silicone oils, and combinations thereof, and wherein the composition has a ratio of the total weight of the water phase to the total weight of the at least one polyglyceryl ester in a range from about 45 to about 70. In some embodiments, the glutamic acid or derivative thereof may be in the oil phase or the water phase. In those embodiments wherein the glutamic acid includes tetrasodium glutamate diacetate, the tetrasodium glutamate diacetate is in the water phase.

In some embodiments of the method the cosmetically acceptable glycol or diol is provided in an amount in a range from about 0.01% to about 10%, by weight, whereby under a given application strain, the creamy emulsion demonstrates breaking and release of the water phase more rapidly as the amount of the cosmetically acceptable glycol or diol is increased within the range.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

The term "break" as used herein refers to the phenomenon of release of the water phase from the oil phase in an inverse (water-in-oil) emulsion and conversion of the emulsion from a thick and creamy to a liquidous state. Breaking is demonstrated and may be measured based on one or more of the extent of release of water phase from the emulsion as detected visually or by measuring the quantity of released water phase, and the change in the fluid properties of the emulsion, either as detected visually/tactilely as a change from more solid like cream to liquid, or rheological measurement. The term "break point" refers to a measurable point at which breaking occurs upon the application of a rubbing force, and in some instances, application of a measurable strain using a testing instrument. As described herein, the break point of an inventive composition may be selected based on the amount of the at least one diol present where increased amount of diol confers a faster break under the same rubbing or strain application as compared with a lesser amount of diol.

The terms "stable" and "stability" with respect to the emulsion architecture of the inventive composition refers to the composition remaining in a creamy emulsion state and not phase separating as evidenced by the formation of significant fluid droplets or pooling of separated phases (e.g., during storage and absent application of force or strain by rubbing on a substrate) and/or maintaining rheological characteristics over time. In some embodiments, stable or stability may include the absence of or minimal formation droplets which indicate release of the internal water phase from the emulsion. Stability is evidenced by one or both of visual inspection and by direct measurement of viscosity. In various embodiments, an inventive composition remains stable at temperatures in the range from about 5° C. to about 45° C. inclusive of the endpoints, over a time period of at least 8 weeks (two months), and may remain stable for longer, for example for at least three months, or at least four months, or at least six months, and up to about at least 3 years, or any value, range, or sub-range therebetween. The exemplified embodiments of the inventive composition shown in the examples herein demonstrated stability at each of 5° C., 25° C., 37° C., and 45° C. for a period of eight weeks. And such exemplified compositions demonstrated stability for 10 freeze-thaw cycles at −20° C./25° C.

The cosmetic composition of the present disclosure is in the form of a creamy emulsion having an internal water phase in an oil phase includes at least one polyglyceryl ester, a glutamic acid, or a derivative thereof, at least one cosmetically acceptable glycol or diol, at least one oil, water, and optionally one or more additives. A water-in-oil emulsion is sometimes referred to as a reverse emulsion. The composition is formulated as a "green" or more "nature-based" composition as compared with comparable compositions, which may contain mineral oil and/or fossil-derived ingredients and leave behind an unpleasant oily and greasy skin feel after use. The composition excludes mineral and organic UV filters. The creamy emulsion demonstrates breaking upon rubbing application of the composition on a substrate. The composition demonstrates stability at temperatures in a range from about 5° C. to about 45° C. for a period of eight weeks and under freeze-thaw conditions that range from about −20° C. to about 25° C., where the stability is evidenced by lack of separation of the water and oil phases in the absence of rubbing on a substrate. The composition according to the disclosure is a water-in-oil emulsion that has a creamy texture.

The inventors developed the inventive composition to address certain deficiencies in the art, including consumer need for compositions that are formulated with sustainable, natural and/or green materials, and in particular that lack or minimize use of non-renewable ingredients (e.g., mineral oil and petrol based ingredients) and ingredients that have negative environmental impact (e.g., EDTA that mobilizes heavy metals). In some embodiments the composition is free or essentially free from non-renewable ingredients and ingredients that have negative environmental impact, and in some particular embodiments excludes or is essentially free from ingredients selected from the group consisting of parabens, phthalates, cyclomethicones, fragrance, silicone, mineral oil, synthetic dyes, gelling agents, sulfates, polyquaternium, microplastics, EDTA, silicone oils, mineral UV filter agents, organic UV filter agents, and combinations thereof. In some embodiments, the composition may include only nominal amounts of petrol based ingredients or may be free from petrol based ingredients.

The inventors also sought to address the deficiencies in the art related to instability of inverse emulsions, particularly those having a large water phase, which are vulnerable to phase separation during typical storage periods or when exposed to freeze thaw cycles. In some embodiments, the inventive composition includes a polyglyceryl ester emulsifier.

It is known to the inventors that Polyglyceryl-4 Diisostearate/Polyhydroxystearate/Sebacate, which is typically used for lightweight, low viscosity cosmetic formulations (not thick, creamy emulsions), is employed and recommended for use in amounts that are greater than 2%.

The inventors have shown in compositions that use of polyglyceryl ester emulsifiers, for example, using Polyglyceryl-4 Diisostearate/Polyhydroxystearate/Sebacate, at a much lower than recommended or typically used amount of less than 2%, that these compositions stably retain essentially all of the large internal phase without separation or pooling but the stability declines over time. The inventors have unexpectedly provided a composition in which inclusion of glutamic acid or a derivative thereof results in sustained stability, as shown in the examples. In addition, the inventors have unexpectedly provided a composition in which inclusion and modulation of the amount of a glycol, in some embodiments a diol, and as exemplified using propanediol allows the point at which the watery transition to be adjusted at a given strain. As shown in the examples, increasing the weight percent amount of propanediol in the composition results in an earlier, more abrupt break during application (at a particular strain) as compared with application of the same composition with lesser amount of the glycol.

Thus, the inventors have demonstrated that the inventive composition forms a robust emulsion that demonstrates freeze/thaw stability and long term (up to 8 weeks) storage stability, while retaining the property of breaking upon rubbing application to a substrate such as skin. Comparative compositions lacking the ingredients of the inventive composition disclosed herein do not meet the tests of material stability, including freeze/thaw and storage stability, as well as water breaking when rubbed on a substrate.

Polyglyceryl Ester Emulsifier

In accordance with the disclosure, embodiments of the composition include at least one polyglyceryl ester emulsifier. In some embodiments, the composition comprises more than one polyglyceryl ester.

The term "Hydrophilic-Lipophilic Balance" or "HLB," refers to an empirical expression for the relationship of the hydrophilic and hydrophobic groups of an emulsifier. This term is well known to those skilled in the art. See, e.g., "The HLB system. A time-saving guide to Emulsifier Selection" (Pub: ICI Americas Inc., 1984) and US2006/0217283 at [0053].

In some embodiments, the at least one polyglyceryl ester emulsifier may have an HLB that is about 10, or less than about 10, and is in some embodiments in a range inclusive of from about 2.5 to about 10, or from about 2.5 to about 9.5, or from about 3 to about 9, and in some examples, the polyglyceryl ester emulsifier has an HLB that is in a range from about 2.5, 2.6, 2.7, 2.8, 2.9, 3, 4, 5, 6, 7, 8, to about 9.9, including increments of about 0.1 therein and therebetween. In some embodiments, the at least one polyglyceryl ester emulsifier may have an HLB that at or greater than about 10. In some embodiments, the composition excludes emulsifiers with an HLB that is about 10, or greater than about 10, including up to or greater than about 15, wherein the composition is devoid or free from, or essentially free from emulsifiers with an HLB that is about 10 or greater than about 10. In some particular embodiments, the composition excludes polyglyceryl ester emulsifiers with an HLB that is about 10. In some embodiments the composition excludes polyglyceryl ester emulsifiers with an HLB that is greater than 10, or in a range from greater than 10 to about 15, or greater than about 15.

In various embodiments, polyglyceryl ester emulsifier may be selected from the group consisting of polyglyceryl-4 diisostearate/polyhydroxystearate/sebacate, polyglyceryl-10 caprate, polyglyceryl-10 caprate, polyglyceryl-10 decastearate, polyglyceryl-10 diisostearate, polyglyceryl-10 dioleate, polyglyceryl-10 distearate, polyglyceryl-10 heptaoleate, polyglyceryl-10 isostearate, polyglyceryl-10 laurate, polyglyceryl-10 myristate, polyglyceryl-10 oleate, polyglyceryl-10 pentaoleate, polyglyceryl-10 pentastearate, polyglyceryl-10 stearate, polyglyceryl-2 caprate, polyglyceryl-2 caprylate, polyglyceryl-2 dipolyhydroxystearate, polyglyceryl-2 laurate, polyglyceryl-2 oleate, polyglyceryl-2 stearate, polyglyceryl-3 caprate, polyglyceryl-3 diisostearate, polyglyceryl-3 methylglucose distearate, polyglyceryl-3 palmitate, polyglyceryl-3 polyricinoleate, polyglyceryl-3 ricinoleate, polyglyceryl-4 caprate, polyglyceryl-4 isostearate, polyglyceryl-4 laurate, polyglyceryl-5 dioleate, polyglyceryl-5 hexastearate, polyglyceryl-5 laurate, polyglyceryl-5 myristate, polyglyceryl-5 oleate, polyglyceryl-5 stearate, polyglyceryl-5 trimyristate, polyglyceryl-5 trioleate, polyglyceryl-6 caprylate, polyglyceryl-6 polyricinoleate, and combinations thereof.

In some embodiments, a suitable polyglyceryl ester may be selected from the group consisting of polyglyceryl-4 diisostearate/polyhydroxystearate/sebacate, polyglyceryl-10 decastearate, polyglyceryl-5 hexastearate, polyglyceryl-10 pentaoleate, polyglyceryl-10 pentastearate, polyglyceryl-10 heptaoleate, polyglyceryl-2 dipolyhydroxystearate, polyglyceryl-4 isostearate, polyglyceryl-6 polyricinoleate, polyglyceryl-3 diisostearate, polyglyceryl-3 ricinoleate, polyglyceryl-5 trioleate, polyglyceryl-2 oleate, polyglyceryl-5 trimyristate, polyglyceryl-2 caprylate, polyglyceryl-2 laurate, polyglyceryl-3 palmitate, polyglyceryl-3 polyricinoleate, polyglyceryl-2 caprate, polyglyceryl-2 stearate, and combinations thereof.

In some embodiments, the at least one polyglyceryl ester is selected from the group consisting of polyglyceryl-4 diisostearate/polyhydroxystearate/sebacate, polyglyceryl-6 polyricinoleate, polyglyceryl-3 diisostearate, polyglyceryl-2 oleate, polyglyceryl-10 laurate, polyglyceryl-3 oleate (and) diisostearoyl polyglyceryl-3 dimer dilinoleate, polyglyceryl-4 isostearate and combinations thereof.

In some embodiments, the at least one polyglyceryl ester emulsifier comprises polyglyceryl-4 diisostearate/ polyhydroxystearate/sebacate.

In some embodiments a suitable polyglyceryl ester emulsifier may be selected from the group consisting of polyglyceryl-10 distearate, polyglyceryl-4 laurate, polyglyceryl-10 diisostearate, polyglyceryl-5 dioleate, polyglyceryl-10 dioleate, polyglyceryl-10 isostearate, polyglyceryl-3 methylglucose distearate, polyglyceryl-10 oleate, polyglyceryl-6 caprylate, polyglyceryl-4 caprate, polyglyceryl-10 myristate, polyglyceryl-10 stearate, polyglyceryl-5 oleate, polyglyceryl-10 laurate, polyglyceryl-5 stearate, polyglyceryl-5 myristate, polyglyceryl-5 la urate, polyglyceryl-10 caprate, polyglyceryl-10 caprate, polyglyceryl-3 caprate, and combinations thereof, wherein the polyglyceryl emulsifier has an HLB that is about 10 or greater than about 10. In some such embodiments, the composition excludes a polyglyceryl emulsifier selected from the group consisting of polyglyceryl-10 distearate, polyglyceryl-4 la urate, polyglyceryl-10 diisostearate, polyglyceryl-5 dioleate, polyglyceryl-10 dioleate, polyglyceryl-10 isostearate, polyglyceryl-3 methylglucose distearate, polyglyceryl-10 oleate, polyglyceryl-6 caprylate, polyglyceryl-4 caprate, polyglyceryl-10 myristate, polyglyceryl-10 stearate, polyglyceryl-5 oleate, polyglyceryl-10 laurate, polyglyceryl-5 stearate, polyglyceryl-5 myristate, polyglyceryl-5 laurate, polyglyceryl-10 caprate, polyglyceryl-10 caprate, polyglyceryl-3 caprate, and combinations thereof.

In various embodiments, each of the at least one polyglyceryl ester is present in the composition at a concentration, from about 0.01% to about 10%, and in some embodiments from about 0.1% to about 5%, and in some embodiments, from about 0.1% to about 2%, from about 0.5% to about 1.5%, or about 1.35%, or any suitable combination, sub-combination, range, or sub-range thereof by weight, based on the weight of the composition. In some embodiments, the composition comprises more than one polyglyceryl ester emulsifier, the combination thereof present in the composition at a concentration, from about 0.01% to about 10%, each of the more than one present in the composition at a concentration from about 0.01% to about 5%, or any suitable combination, sub-combination, range, or sub-range thereof by weight, based on the weight of the composition. One of ordinary skill in the art, however, will appreciate that other ranges are within the scope of the invention.

In some representative examples, a polyglyceryl ester co-emulsifier comprising polyglyceryl-6 polyricinoleate may be present in the composition in a range from about 0.1% to about 1% or at about 0.2%.

Thus, in various embodiments, each of the at least one polyglyceryl ester emulsifier is present in a composition according to the disclosure from about 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, to about 10 percent by weight, including increments and ranges there between.

Glutamic Acid, or a Derivative Thereof

In accordance with the disclosure, embodiments of the composition include at least one glutamic acid or derivative thereof. In some embodiments, the composition comprises more than glutamic acid or derivative thereof.

In various embodiments, the glutamic acid or derivative thereof is selected from the group consisting of tetrasodium glutamate diacetate, lauroyl glutamic acid, myristoyl glutamic acid, palmitoyl glutamic acid, stearoyl glutamic acid, behenoyl glutamic acid, olivoyl glutamic acid, cocoyl glutamic acid, the salts thereof, and combinations thereof.

In some particular embodiments the glutamic acid or derivative thereof comprises tetrasodium glutamate diacetate.

In various embodiments, the glutamic acid, or a derivative thereof is present from about 0.01% to about 5%, by weight of the composition, or from about 0.1% to about 1.5%, and in some embodiments, from about 0.4% to about 1.2%, and in some embodiments, from about 0.4% to about 1%, and in some embodiments from about 0.5% to about 0.9%, or about 0.8%, or any suitable combination, sub-combination, range, or sub-range thereof by weight, based on the weight of the composition. One of ordinary skill in the art, however, will appreciate that other ranges are within the scope of the invention.

Thus, in various embodiments, the glutamic acid, or a derivative thereof is present in a composition according to the disclosure from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, to about 5 percent, by weight, including increments and ranges therein and there between.

Cosmetically Acceptable Glycol or Diol

In accordance with the disclosure, embodiments of the composition include at least one cosmetically acceptable glycol or diol. In some embodiments the at least one cosmetically acceptable glycol or diol is a diol, and in some particular embodiments an alkane diol. In some embodiments, the composition comprises more than one cosmetically acceptable glycol or diol.

In some embodiments, the at least one cosmetically acceptable glycol or diol is a diol selected from the group consisting of propanediol, ethylene glycol, propylene glycol, butylene glycol, pentylene glycol, hexylene glycol, decylene glycol, 1,2-butanediol, 1,2-heaxanediol, caprylyl glycol, ethyl hexanediol and combinations thereof.

In some particular embodiments, the at least one cosmetically acceptable glycol or diol comprises propanediol.

In various embodiments, the at least one cosmetically acceptable glycol or diol is present from about 0.01% to about 10% by weight of the composition, and in some embodiments, from about 0.8% to about 8%, and in some embodiments, from about 1% to about 7%, and in some embodiments, from about 2% to about 5%, and in some embodiments, about 5% or about 2%, or any suitable combination, sub-combination, range, or sub-range thereof by weight, based on the weight of the composition. One of ordinary skill in the art, however, will appreciate that other ranges are within the scope of the invention.

Thus, in various embodiments, each one or a combination of at least one cosmetically acceptable glycol or diol is present in a composition according to the disclosure from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, to about 10 percent, by weight, including increments and ranges therein and there between.

OH

In accordance with the various embodiments, the composition includes at least one oil. In some embodiments the at least one oil is a water-immiscible oil. In some embodiments the at least one oil may include more than one oil. In some embodiments the at least one oil is selected from the group consisting of butters, waxes and hydrocarbon-based oils from plants or of plant origin.

In some embodiments, an oil may be chosen from squalane, purcellin oil (cetostearyl octanoate), hemisqualane, isononyl isononanoate, C12 to C15 alkyl benzoate, 2-ethylhexyl palmitate, isodecyl neopentanoate, tridecyl neopentanoate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate and 2-diethylhexyl succinate, cocoglyceride, cyclomethicone, dimethicone, dicaprylyl carbonate, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of C9-C15 alcohols, alkanes, mineral oil, silicone, dimethyl polysiloxane, ether, polyoxypropylene butyl ether, polyoxypropylene cetyl ether, C12-C15 alkyl benzoate, aryl alkyl benzoate, Isopropyl Lauroyl sarcosinate, and any combinations thereof. In some embodiments, an oil may be chosen Isopropyl myristate, dicaprylyl ether, ethylhexyl palmitate, Isopropyl palmitate, cetearyl ethylhexanoate, Isononyl isononanoate, isopropyl isostearate, diisopropyl sebacate, coco caprylate/caprate, diisopropyl adipate, isohexadecane, C15-19 alkane, isododecane, undecane, tridecane, dodecane, and combinations thereof. In some embodiments, silicone, synthetic and petroleum based oils are excluded. In some specific embodiments, the composition excludes mineral oil, silicone oil, petroleum based oil, or a combination thereof.

In accordance with the various embodiments, the at least one oil is present from about 0.01% to about 20%. One of ordinary skill in the art, however, will appreciate that other ranges are within the scope of the invention.

In accordance with some embodiments, the composition may comprise at least one plant butter, the at least one butter selected from the group consisting of Butyrospermum Parkii (Shea) Butter, theobroma cacao (cocoa) seed butter, almond butter, aloe butter, apricot kernel butter, avocado butter, coconut cream butter, cupuacu butter, dhupu butter, hemp butter, jojoba butter, kokum butter, macadamia nut butter, mango butter and combinations thereof. In some embodiments, the at least one butter has a melting point in the range of from about 30 to about 45 degrees Celsius.

In some embodiments, the at least one oil comprises at least one wax. In some particular embodiments, the at least one wax is selected from the group consisting of Copernicia Cerifera (Carnauba) Wax, candelilla wax, sunflower wax and combinations thereof.

In some embodiments, the at least one oil may be chosen from Butyrospermum Parkii (Shea) Butter, Copernicia Cerifera (Carnauba) Wax, Persea Gratissima (avocado) oil, squalane, and combinations thereof.

In an exemplary embodiment, the at least one oil comprises a blend comprising Butyrospermum Parkii (Shea) Butter, Copernicia Cerifera (Carnauba) Wax, Persea Gratissima (avocado) oil, and squalane.

In some embodiments, the at least one oil may be present in a range from about 0.01% to about 23%, or from about 1% to about 12%, or from about 1% to about 10%, or from about 2% to about 8%, or any suitable combination, sub-combination, range, or sub-range thereof by weight, based on the weight of the composition. One of ordinary skill in the art, however, will appreciate that other ranges are within the scope of the invention.

In some embodiments, the amount of plant butter, when present in the composition may be at least 1%, alternatively from about 1% to about 23%; alternatively, from about 2% to about 9%, alternatively from about 3% to about 8%, alternatively from about 4% to about 7%, alternatively from about 5% to about 6%, or any suitable combination, sub-combination, range, or sub-range thereof by weight, based on the weight of the composition. One of ordinary skill in the art, however, will appreciate that other ranges are within the scope of the invention.

In some embodiments, the amount of wax, when present in the composition may be from about 0.05% to about 5%, or from about 0.05% to about 1%, or 0.1% or any suitable combination, sub-combination, range, or sub-range thereof by weight, based on the weight of the composition. One of ordinary skill in the art, however, will appreciate that other ranges are within the scope of the invention.

Thus, any one of or a combination of oil is present, by weight, based on the total weight of the composition, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16,17, 18, 19 to about 20 weight percent, including increments and ranges therein and there between.

Water

In accordance with various embodiments, the composition includes a water phase that is present in an range from about 75% to about 95%, wherein the water phase includes water, or water and a water-based hydrating agent or solvent or combination thereof, the at least one cosmetically acceptable glycol or diol, and any optional suitable water phase additives.

In accordance with the various embodiments, water, or water and a water-based hydrating agent or solvent or combination thereof is present in the composition. In some embodiments, water is present in a range from about 65% to about 95%, and in some embodiments, from about 60% to about 85%, and in some embodiments, from about 70% to about 80%, and in some embodiments, from about 70% to about 77% or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, to about 95 percent, by weight, including increments and ranges therein and there between. One of ordinary skill in the art, however, will appreciate that other ranges are within the scope of the invention.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition, in particular the water phase of the composition, may be adjusted prior to combining the oil phase with the water phase to avoid the practical difficulty with measuring pH in an internal water phase of the water-in-oil emulsion. In various embodiments, the pH is a physiologically acceptable pH. In some embodiments, the pH of the water phase prior to emulsification can be adjusted with pH adjusters to a pH in a range from about 5 to about 6 by addition of a base (organic or inorganic) to the composition, for example sodium hydroxide, ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Hydrating Agents and Solvents

In accordance with the disclosure, embodiments of the composition may include at least one hydrating agent, at least one solvent, or a combination thereof. In some embodiments, the composition comprises more than one hydrating agent, more than one solvent, or a combination thereof. The hydrating agent may be a polyol. In some embodiments, the hydrating agent comprises glycerin.

In some embodiments, suitable hydrating agents that may be used according to the disclosure may be chosen from one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, diethylene glycol, diethylene glycol, hexylene glycol; glycol ethers such as monopropylene, dipropylene and tripropylene glycol alkyl(C1-C4)ethers; squalane; triacetin; sugars, such as glucose, xylitol, maltitol, sorbitol, sucrose pentaerythritol, inositol; pyrrolidone carboxylic acid (PCA); lactic acid; lithium chloride; acetamide MEA; sodium lactate; urea; dicyanamide; hyaluronic acid; aloe vera; honey; seaweed extract; and combinations thereof.

In some embodiments, suitable solvents that may be used according to the disclosure may be chosen from monoalcohols and polyols, such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

In various embodiments, the at least one hydrating agent, solvent or combination thereof, is present from about 1% to about 20% by weight of the composition, and in some embodiments, from about 2% to about 15%, and in some embodiments, from about 3% to about 10%, from about 4% to about 8%, and in some embodiments, about 5%, or any suitable combination, sub-combination, range, or sub-range thereof by weight, based on the weight of the composition. In some embodiments, the composition comprises more than one hydrating agent, solvent or combination thereof, the combination thereof present in the composition at a concentration, from about 1% to about 20%, and in some embodiments, about 5% or any suitable combination, sub-combination, range, or sub-range thereof, by weight, based on the weight of the composition. One of ordinary skill in the art, however, will appreciate that other ranges are within the scope of the invention.

Thus, in various embodiments, each of the at least one hydrating agent, solvent or combination thereof is present in a composition according to the disclosure from about 1, 2, 3, 4, 5, 6, 7, 8, 9, 10, 11, 12, 13, 14, 15, 16, 17, 18, 19, to about 20 percent, by weight, including increments and ranges therein and there between.

Optional Additives

The composition may also comprise at least one additive used in the cosmetics field which does not affect the properties of the compositions according to the invention, such as fragrances, preservatives/anti-microbials (for example, chlorphenesin, salicylic acid, phenoxyethanol, potassium sorbate, and caprylyl glycol); actives (for example, hydroxyacetophenone, vitamins, panthenol, tocopherol); oil-soluble active ingredients (for example, vitamin A, beta carotene, tocopherol/vitamin E) and emollients; coloring materials/pigments; essential oils; antioxidants; hydroxy acids; citric acid, sodium citrate, sodium chloride; neutralizing, chelating or pH-adjusting agents (for example, triethylamine (TEA), trisodium ethylenediamine disuccinate, EDTA, and sodium hydroxide), and combinations thereof. In some particular examples, the oil phase may further comprise oil soluble actives selected from the group consisting of vitamin E, vitamin A, beta carotene, retinol, resveratrol, derivatives thereof, and combinations thereof. And in some particular examples, the water phase may further comprise water soluble actives selected from the group consisting of vitamin C, niacinamide, derivatives thereof, and combinations thereof.

In some embodiments the composition may comprise at least one additive selected from the group consisting of pH adjusters, chelating agents, skin care actives, preservatives, fillers, powders, fragrances, dyes, pigments, and combinations thereof. In some particular embodiments the composition may comprise at least one additive selected from the group consisting of sodium dehydroacetate, salicylic acid, phenoxyethanol, chromium oxide greens, sodium PCA, copper gluconate, sodium chloride, tocopherol, caffeine, beta-carotene (beta carotene or other provitamin A carotenoid, or retinol), citric acid, and combinations thereof.

Although the optional additives are given as examples, it will be appreciated that other optional components compatible with cosmetic applications known in the art may be used that are suitable for a cosmetic composition.

In accordance with the various embodiments, the amount of one or more actives and additives, alone or in combination, when present in the composition according to the disclosure can be present in a range from about 0.0001% to about 20%, and in some embodiments, from about 0.005% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5% and in some embodiments, from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of actives and additives may be present, each one or the combination present from about 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

The examples below according to the invention are given by way of illustration and without a limiting nature. The names are the chemical name or the INCI name. The amounts are given therein as % by weight, unless otherwise mentioned.

EXAMPLES

Example 1: Compositions

Various representative embodiments of inventive and comparative compositions are exemplified herein.

TABLE 1

Inventive Compositions 1-2 and Comparative Compositions 1-3

| Ingredient | Inv 1 | Inv 2 | Comp 1 | Comp 2 | Comp 3 |
|---|---|---|---|---|---|
| *Butyrospermum Parkii* (Shea) Butter | 3.00 | 3.00 | 4.00 | 3.00 | 3.00 |
| *Copernicia Cerifera* (Carnauba) Wax | 0.10 | 0.10 | | 0.10 | 0.10 |
| *Persea Gratissima* (Avocado) Oil | 3.50 | 3.50 | | 3.50 | 3.50 |
| Squalane | 6.50 | 6.50 | | 5.00 | 6.50 |
| Glycerin | 5.00 | 5.00 | | 5.00 | 5.00 |
| Polyglyceryl-4 Diisostearate/Polyhydroxystearate/Sebacate | 1.35 | 1.35 | | 1.35 | 1.35 |
| Propanediol | 1.60 | 5.00 | | 1.60 | 1.60 |
| *Tetrasodium Glutamate Diacetate | 0.80 | 0.80 | | | |
| Sodium Chloride, Sodium Dehydroacetate, Salicylic Acid, Chromium Oxide Greens, Sodium PCA | | | | 1.68 | |
| Copper Gluconate, Sodium Chloride, Sodium Dehydroacetate, Salicylic Acid, Chromium Oxide Greens, Sodium PCA | 1.69 | 1.69 | | | 1.69 |
| Sodium Hydroxide | | | | 0.025 | 0.03 |
| Sorbitan Sesquioleate, Isopropyl Palmitate, Butylene Glycol, *Persea Gratissima* (Avocado) Oil, Hydrogenated Castor Oil, Propylene Glycol, Isocetyl Stearoyl Stearate, Hydrogenated Jojoba Oil, Peg-30 Dipolyhydroxystearate, Tridecyl Stearate (And) Tridecyl Trimellitate (And) Dipentaerythrityl Hexacaprylate/Hexacaprate, Magnesium Sulfate, Tocopheryl Acetate, Disodium EDTA, Phenoxyethanol, Chlorphenesin, Isodecyl Salicylate, P-Anisic Acid, Copper PCA, Beta-Carotene, Sodium PCA | | | 23.8 | | |
| Isopropyl Isostearate | | | | 1.50 | |
| Tocopherol, Beta-Carotene, Caffeine | | | | 0.61 | 0.61 |

TABLE 1-continued

Inventive Compositions 1-2 and Comparative Compositions 1-3

| Ingredient | Inv 1 | Inv 2 | Comp 1 | Comp 2 | Comp 3 |
| --- | --- | --- | --- | --- | --- |
| Tocopherol, Beta-Carotene, Citric Acid, Caffeine | 0.66 | 0.66 | | | |
| Water | 75.80 | 72.40 | 72.19 | 76.74 | 76.62 |

*Glutamic acid derivative is 47.5% active

Comparative compositions 1-4 were employed together with the Inventives in studies as shown in the examples, below, wherein Comp 1 has a different general formulation and lacks the polyglyceryl ester emulsifier and includes a different emulsifier, lacks propanediol and lacks glutamate or derivative. Comp 2 and 3 have a similar base to Inventive Compositions 1 and 2 but lack the glutamate or derivative.

In preparing the inventive composition examples, water phase (A) ingredients are mixed separately from oil phase (B) ingredients which are blended under heating then added in batch to the water phase and blended followed by measurement of viscosity.

In a representative embodiment according to the disclosure the composition includes polyglyceryl-4 diisostearate/polyhydroxystearate/sebacate present at about 1.35%; tetrasodium glutamate diacetate present at about 0.8%; propanediol present at about 1.6% or about 5%; Butyrospermum Parkii (Shea) Butter present at about 3%, Copernicia Cerifera (Carnauba) Wax present at about 0.1%, Persea Gratissima (avocado) oil present at about 3.5%, squalane present at about 6.5%, more generally, each present from about 0.1% to about 23%; water present at about 70% to about 76%, and glycerin present at about 5%, all amounts by weight of the composition. The composition also includes sodium dehydroacetate, salicylic acid, chromium oxide greens, sodium PCA, copper gluconate, sodium chloride, tocopherol, caffeine, beta-carotene, and citric acid. The composition is a creamy water-in oil emulsion comprising (a) a water phase that comprises the water, or water and a water-based hydrating agent or solvent or combination thereof, and the at least one cosmetically acceptable glycol or diol, and (b) an oil phase comprising the at least one polyglyceryl ester, in some embodiments the glutamic acid, or a derivative thereof, and the at least one oil. The composition has a ratio of the total weight of the water phase to the total weight of the at least one polyglyceryl ester in a range from about 45 to about 70. In some embodiments, the glutamic acid or derivative thereof may be in the oil phase or the water phase. In those embodiments wherein the glutamic acid includes tetrasodium glutamate diacetate, the tetrasodium glutamate diacetate is in the water phase.

Example 2: Freeze-Thaw Stability

Referring to TABLE 1, the shown Inventive and Comparative compositions were exposed to 10 freeze-thaw cycles of −20° C./+25° C.

Only the Inventive compositions were stable under these conditions.

Comparative compositions 2 and 3, both lacking the glutamate or derivative, showed minor separation. Comparative composition 1 lacking the polyglyceryl ester emulsifier, propanediol and glutamate or derivative, showed separation.

Example 3: Heat Stability

Referring again to TABLE 1, the shown Inventive and Comparative compositions were exposed to 2 months at 25° C. and 45° C.

Comparative composition 1 lacking the polyglyceryl ester emulsifier, propanediol and glutamate or derivative showed separation under 45° C. conditions. This formula also showed separation at longer term evaluation at room temperature (approximately 6 months).

Comparative composition 2, lacking the glutamate or derivative, did not show separation under 45° C. conditions; however, it was not stable due to the softening of texture to a lotion instead of a substantially thick cream.

Example 4: Quantifying the Transitioning Texture

Rheology studies were conducted to quantify the unique transitioning texture of inventive compositions. Tested compositions were evaluated at their initial time point as well as after 2 months for stability at 25° C. and 45° C. for breaking and rheological properties. Comparative composition 1 lacking the polyglyceryl ester emulsifier, propanediol and glutamate or derivative showed softening over time and an earlier break, leading to its eventual instability of separation as shown in Examples 2 and 3. The Inventive compositions demonstrated stability over time and maintained their initial break point and rheological properties over time. Inventive Composition 1, with the lesser amount of the cosmetically acceptable glycol or diol, demonstrated breaking at a higher strain (i.e., requiring longer duration of rubbing prior to break) than Inventive Composition 2 with a greater amount of the glycol. This study demonstrated that in a composition according to the disclosure, propanediol may be used to adjust the break point of a composition. Thus, an inventive composition may be designed to require more or less rubbing of the composition on application before the emulsion will thin and release the water phase, wherein a greater amount of propanediol allows for an earlier transition by requiring less strain for the transformation as compared with the same composition having a lesser amount of propanediol applied with the same force or strain.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more than one, including two or more than two, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

The term "about," means within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. A range given of "about 1% to 10%" is intended to have the term "about" modifying both the 1% and the 10% endpoints. Further, a range is intended to be inclusive of the endpoints of and all numbers in the range except as expressly stated otherwise. Further still, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A cosmetic composition, consisting of:
a creamy emulsion having an internal water phase in an oil phase, the creamy emulsion consisting of:
   i. at least one polyglyceryl ester present from about 0.01% to and not more than about 2%, by weight of the cosmetic composition;
   ii. a glutamic ingredient selected from the group consisting of glutamic acid, tetrasodium glutamate diacetate, lauroyl glutamic acid, myristoyl glutamic acid, palmitoyl glutamic acid, stearoyl glutamic acid, behenoyl glutamic acid, olivoyl glutamic acid, cocoyl glutamic acid, salts thereof, and combinations thereof, the glutamic ingredient present from at least about 0.5% to about 1.5%, by weight of the cosmetic composition;
   iii. at least one cosmetically acceptable glycol or diol present from about 0.01% to about 10%, by weight of the cosmetic composition;
   iv. at least one oil present from about 0.1% to about 23%, by weight of the cosmetic composition;
   v. water, or water and a water-based hydrating agent or solvent or combination thereof present from about 65% to about 95% by weight of the cosmetic composition; and,
   vi. optionally one or more additives selected from the group consisting of oil-soluble active ingredients, emollients, silicone oils, pH adjusters, chelating agents, skin care actives, fillers, powders, fragrances, dyes, pigments, coloring materials, chlorphenesin, sodium dehydroacetate, salicylic acid, phenoxyethanol, potassium sorbate, caprylyl glycol, chromium oxide greens, sodium PCA, copper gluconate, sodium chloride, tocopherol, caffeine, beta-carotene, provitamin A carotenoid, retinol, citric acid, hydroxyacetophenone, vitamins, vitamin A, vitamin C, vitamin E, panthenol, essential oils, antioxidants; hydroxy acids, sodium citrate, neutralizing agents, pH-adjusting agents, triethylamine, trisodium ethylenediamine disuccinate, EDTA, sodium hydroxide, retinol, resveratrol, niacinamide, and combinations thereof, wherein the creamy emulsion demonstrates breaking and release of the water phase upon rubbing application of the cosmetic composition on a substrate, and wherein the cosmetic composition demonstrates stability at temperatures in a range from about 5° C. to about 45° C. for a period of eight weeks and under freeze-thaw conditions that range from about −20° C. to about 25° C., stability evidenced by lack of separation of the water and oil phases in the absence of rubbing on a substrate.

2. The cosmetic composition according to claim 1, wherein the at least one polyglyceryl ester is present from about 0.5% to about 1.5%, by weight of the cosmetic composition.

3. The cosmetic composition according to claim 1, wherein the glutamic ingredient is present from about 0.8% to about 1% by weight of the cosmetic composition.

4. The cosmetic composition according to claim 1, wherein the at least one cosmetically acceptable glycol or diol is present from about 1% to about 7% by weight of the cosmetic composition.

5. The cosmetic composition according to claim 1, wherein the at least one oil is present from about 2% to about 17%, by weight of the cosmetic composition.

6. The cosmetic composition according to claim 1, wherein the cosmetically acceptable glycol or diol is present in an amount in a range from about 2% to about 5%, by weight of the cosmetic composition, whereby under a given application strain, the creamy emulsion demonstrates breaking and release of the water phase more rapidly as the amount of the cosmetically acceptable glycol or diol is increased within the range.

7. The cosmetic composition according to claim 1, wherein the water, or the water and the water-based hydrating agent or the solvent or combination thereof is present from about 75% to about 95% by weight of the cosmetic composition, and wherein, when present, the water-based hydrating agent is present from about 1% to about 20% by weight of the cosmetic composition.

8. The cosmetic composition according to claim 1, wherein the cosmetic composition is a creamy water-in-oil emulsion consisting of:
(a) a water phase that has:
the water, or the water and the water-based hydrating agent or the solvent or combination thereof; and
the at least one cosmetically acceptable glycol or diol;
the water phase being present in a range of from about 75% to about 95% by weight, based on the weight of the cosmetic composition; and
(b) an oil phase that has:
the at least one polyglyceryl ester and the at least one oil,
wherein one of the water phase and the oil phase also has the tetrasodium glutamate diacetate, and
wherein the cosmetic composition has a ratio of the total weight of the water phase to the total weight of the at least one polyglyceryl ester in the cosmetic composition in a range from about 45 to about 70.

9. The cosmetic composition according to claim 8, wherein the oil phase further has the oil-soluble active ingredients, the emollients, the silicone oils, or combinations thereof, and one or both the water phase and oil phase optionally has the pH adjusters, the chelating agents, the skin care actives, the chlorphenesin, the sodium dehydroacetate, the salicylic acid, the phenoxyethanol, the potassium sorbate, the caprylyl glycol, the fillers, the powders, the fragrances, the dyes, the pigments, or combinations thereof.

10. The cosmetic composition according to claim 1, wherein:
i. the at least one polyglyceryl ester is present from about 0.5% to and not more than about 1.5%, by weight of the cosmetic composition;
ii. the glutamic ingredient is present from at least about 0.5% to about 1%, by weight of the cosmetic composition;
iii. the at least one cosmetically acceptable glycol or diol is present from about 1% to about 7%, by weight of the cosmetic composition;
iv. the at least one oil is present from about 2% to about 17%, by weight of the cosmetic composition;
v. the water, or the water and the water-based hydrating agent or the solvent or combination thereof is present from about 75% to about 95% by weight of the cosmetic composition; and,
vi. the optionally one or more additives is selected from the group consisting of the pH adjusters, the chelating agents, the skin care actives, the chlorphenesin, the sodium dehydroacetate, the salicylic acid, the phenoxyethanol, the potassium sorbate, the caprylyl glycol, the fillers, the powders, the fragrances, the dyes, the pigments, and combinations thereof.

11. The cosmetic composition according to claim 1, wherein:
i. the at least one polyglyceryl ester is selected from the group consisting of polyglyceryl-4 diisostearate/polyhydroxystearate/sebacate, polyglyceryl-6 polyricinoleate, polyglyceryl-3 diisostearate, polyglyceryl-2 oleate, polyglyceryl-10 laurate, polyglyceryl-3 oleate and diisostearoyl polyglyceryl-3 dimer dilinoleate, polyglyceryl-4 isostearate and combinations thereof;
ii. the at least one cosmetically acceptable glycol or diol is selected from the group consisting of propanediol, ethylene glycol, propylene glycol, butylene glycol, pentylene glycol, hexylene glycol, decylene glycol, 1, 2-butanediol, 1,2-heaxanediol, caprylyl glycol, ethyl hexanediol and combinations thereof; and
iii. the at least one oil is selected from the group consisting of Butyrospermum Parkii (Shea) Butter, Copernicia Cerifera (Carnauba) Wax, Persea Gratissima (avocado) oil, squalane, and combinations thereof.

12. The cosmetic composition according to claim 10, wherein:
the at least one polyglyceryl ester is polyglyceryl-4 diisostearate/polyhydroxystearate/sebacate;
the glutamic ingredient is present in the water phase;
the at least one cosmetically acceptable glycol or diol is propanediol; and
the at least one oil is a combination of Butyrospermum Parkii (Shea) Butter, Copernicia Cerifera (Carnauba) Wax, Persea Gratissima (avocado) oil, and squalane; and
the water and the water-based hydrating agent are present, the water-based hydrating agent being present from about 1% to about 20% by weight of the cosmetic composition.

13. The cosmetic composition according to claim 10, wherein:
the at least one polyglyceryl ester is polyglyceryl-4 diisostearate/polyhydroxystearate/sebacate present at about 1.35%, by weight of the cosmetic composition;
the glutamic ingredient is present at about 0.8% in the water phase, by weight of the cosmetic composition;

the at least one cosmetically acceptable glycol or diol is propanediol present from about 1.6% to about 5%, by weight of the cosmetic composition;

the at least one oil is a combination of Butyrospermum Parkii (Shea) Butter, Copernicia Cerifera (Carnauba) Wax, Persea Gratissima (avocado) oil, and squalane;

the water and the water-based hydrating agent are present, and glycerin is the water-based hydrating agent present at about 5%, by weight of the cosmetic composition; and the one or more additives has the sodium dehydroacetate, the salicylic acid, the phenoxyethanol, the chromium oxide greens, the sodium PCA, the copper gluconate, the sodium chloride, the tocopherol, the caffeine, the beta-carotene, the retinol, the citric acid, or combinations thereof.

14. The cosmetic composition according to claim 1, wherein the glutamic ingredient is present from about 0.8% to about 1%, by weight of the cosmetic composition.

15. A cosmetic composition, comprising:
a creamy emulsion having an internal water phase in an oil phase, the creamy emulsion comprising:
   i. at least one polyglyceryl ester present from about 0.01% to and not more than about 2%, by weight of the cosmetic composition, the at least one polyglyceryl ester being selected from the group consisting of polyglyceryl-4 diisostearate/polyhydroxystearate/sebacate, polyglyceryl-6 polyricinoleate, polyglyceryl-3 diisostearate, polyglyceryl-2 oleate, polyglyceryl-10 laurate, polyglyceryl-3 oleate (and) diisostearoyl polyglyceryl-3 dimer dilinoleate, polyglyceryl-4 isostearate and combinations thereof;
   ii. a glutamic ingredient present from at least about 0.8% to about 1%, by weight of the cosmetic composition, the glutamic ingredient including tetrasodium glutamate diacetate and, optionally, glutamic acid, lauroyl glutamic acid, myristoyl glutamic acid, palmitoyl glutamic acid, stearoyl glutamic acid, behenoyl glutamic acid, olivoyl glutamic acid, cocoyl glutamic acid, salts thereof, or combinations thereof;
   iii. at least one cosmetically acceptable glycol or diol present from about 0.01% to about 10%, by weight of the cosmetic composition, the at least one cosmetically acceptable glycol or diol being selected from the group consisting of propanediol, ethylene glycol, propylene glycol, butylene glycol, pentylene glycol, hexylene glycol, decylene glycol, 1, 2-butanediol, 1,2-heaxanediol, caprylyl glycol, ethyl hexanediol and combinations thereof;
   iv. at least one oil present from about 0.1% to about 23%, by weight of the cosmetic composition, the at least one oil being selected from the group consisting of Butyrospermum Parkii (Shea) Butter, Copernicia Cerifera (Carnauba) Wax, Persea Gratissima (avocado) oil, squalane, and combinations thereof;
   v. water, or water and a water-based hydrating agent or solvent or combination thereof present from about 65% to about 95% by weight of the cosmetic composition; and,
   vi. optionally one or more additives,
wherein the cosmetic composition excludes mineral and organic UV filters, and wherein the creamy emulsion demonstrates breaking and release of the water phase upon rubbing application of the cosmetic composition on a substrate, and wherein the cosmetic composition demonstrates stability at temperatures in a range from about 5° C. to about 45° C. for a period of eight weeks and under freeze-thaw conditions that range from about −20° C. to about 25° C., stability evidenced by lack of separation of the water and oil phases in the absence of rubbing on a substrate.

16. The cosmetic composition according to claim 15, wherein:
   i. the at least one polyglyceryl ester is present from about 0.5% to and not more than about 1.5%, by weight of the cosmetic composition;
   ii. the at least one cosmetically acceptable glycol or diol is present from about 1% to about 7%, by weight of the cosmetic composition; and
   the at least one oil is present from about 2% to about 17%, by weight of the cosmetic composition.

17. The cosmetic composition according to claim 16, wherein the tetrasodium glutamate diacetate is present at about 0.8%, by weight of the cosmetic composition.

18. A method for applying a water breaking cosmetic composition, comprising applying the cosmetic composition of claim 1 to a keratinous substrate and rubbing in a circular motion whereby the creamy emulsion demonstrates breaking and release of the water phase.

19. The method according to claim 18, wherein;
the at least one polyglyceryl ester is polyglyceryl-4 diisostearate/polyhydroxystearate/sebacate present at about 1.35%, by weight of the cosmetic composition;
the glutamic ingredient is present at about 0.8%, by weight of the cosmetic composition;
the at least one cosmetically acceptable glycol or diol is propanediol present at about 1.6% to about 5%, by weight of the cosmetic composition;
the at least one oil is present from about 0.1% to about 23%, by weight of the cosmetic composition;
the water and the water-based hydrating agent are present and glycerin is the water-based hydrating agent present at about 5%, by weight of the cosmetic composition;
the one or more additives has the sodium dehydroacetate, the salicylic acid, the phenoxyethanol, the chromium oxide greens, the sodium PCA, copper gluconate, the sodium chloride, the tocopherol, the caffeine, the beta-carotene, the retinol, the citric acid, or combinations thereof; and
the cosmetic composition is a creamy water-in oil emulsion consisting of:
   (a) a water phase that has:
      the water, or water and a water-based hydrating agent or solvent or combination thereof;
      the glutamic ingredient; and
      the at least one cosmetically acceptable glycol or diol; and
   (b) an oil phase that has:
      the at least one polyglyceryl ester; and
      the at least one oil,
   wherein the cosmetic composition has a ratio of the total weight of the water phase to the total weight of the at least one polyglyceryl ester in a range from about 45 to about 70, and
   wherein the oil phase has the silicone oils, the oil-soluble active ingredients, the emollients, or combinations thereof.

* * * * *